Figure 1:
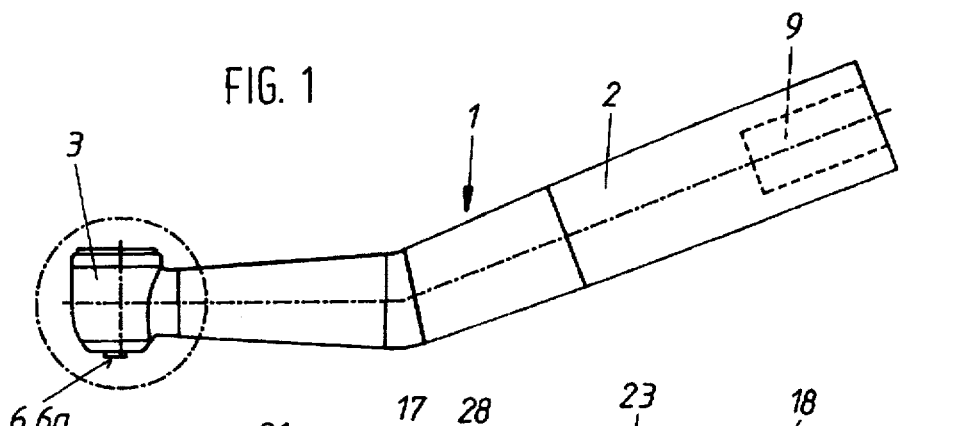

United States Patent
Lingenhöle et al.

[11] Patent Number: 5,676,542
[45] Date of Patent: Oct. 14, 1997

[54] MEDICAL OR DENTAL TREATMENT INSTRUMENT

[75] Inventors: Bernhard Lingenhöle, Warthausen; Eugen Mohr, Ummendorf, both of Germany

[73] Assignee: Kaltenbach & Voigt GmbH & Co., Bieberach, Germany

[21] Appl. No.: 494,080

[22] Filed: Jun. 23, 1995

[30] Foreign Application Priority Data

Jul. 1, 1994 [DE] Germany ............. 44 23 222.5

[51] Int. Cl.$^6$ ......................................... A61C 1/05
[52] U.S. Cl. ................................. 433/115; 433/132
[58] Field of Search ...................... 433/115, 132; 415/904

[56] References Cited

U.S. PATENT DOCUMENTS 5,423,678  6/1995  Nakanishi ..................... 433/132

FOREIGN PATENT DOCUMENTS 527473   2/1993   European Pat. Off. .
37 19 149  12/1988  Germany .

Primary Examiner—Cary E. O'Connor
Attorney, Agent, or Firm—Marshall, O'Toole, Gerstein, Murray & Borun

[57] ABSTRACT

In a medical or dental treatment instrument, in particular a straight or angled handpiece (1), having a drive shaft (6) for a tool, which drive shaft is mounted in the forward end region of the treatment instrument, in at least one roller bearing (11, 12), rotatable around its middle axis (8), and is drivable for example by a turbine, whereby the roller bearing (11, 12) is blocked or sealed against contaminants with of a blocking ring (31) effective between its outer ring (37) and its inner ring (34). The blocking ring (31) bears with its surface facing the inner ring (34) on the inner ring (34) and is releasibly or non-releasibly attached thereon.

22 Claims, 4 Drawing Sheets

MEDICAL OR DENTAL TREATMENT INSTRUMENT

The invention relates to a medical or dental treatment instrument according to the preamble of claim 1, 2, 3 or 7.

The bearings of a drive shaft of a medical or dental treatment instrument or of a handpiece for a, in particular, medical laboratory, are subject to considerable loads in operation, which loads are inter alia the result of the relatively high speeds of rotation with which both electrically and also in particular pneumatically driven drive shafts rotate. In particular in the higher range of speeds of rotation, the entry of contaminant materials, in particular into the bearing near the tool, is to be prevented, since otherwise the contaminant material leads to premature wear and failure of the bearing and thus of the treatment instrument. As contaminant materials there must be considered, inter alia, in particular both treatment fluids such as water, spray or also body fluids such as blood and saliva. It is thereby to be taken into consideration that there are various functional criteria which favour the movement of the contaminant materials on the drive shaft towards the bearing, for example upon cleaning of the treatment site with water and/or compressed air, for example spray, during treatment operation, whereby such a treatment fluid reflected from the treatment site can easily enter into the housing of the treatment instrument and penetrate further to the location of the bearing.

The bearing problem under consideration presents itself in particular with such treatment instruments the drive shaft of which is driven by means of a turbine the turbine wheel of which sits on the drive shaft, in most cases between two roller bearings. With such a turbine drive, the turbine wheel exercises a suction effect as it is running out after switching off of the compressed gas (air), which suction effect leads to an axial suction flow on the drive shaft to the two sides of the turbine wheel. Such a suction flow encourages the movement of contaminant materials towards the locations of the bearings.

For the purpose of sealing the roller bearings of an above-described turbine handpiece, there has already been associated with the roller bearings a particular sealing disk for sealing the gap between the inner ring and the outer ring. Such a configuration is provided in the Assignee's tried and tested turbine handpieces which are on the market. This known configuration will be described in more detail below with reference to FIGS. 7 and 8 of the accompanying drawings.

Figure 7:
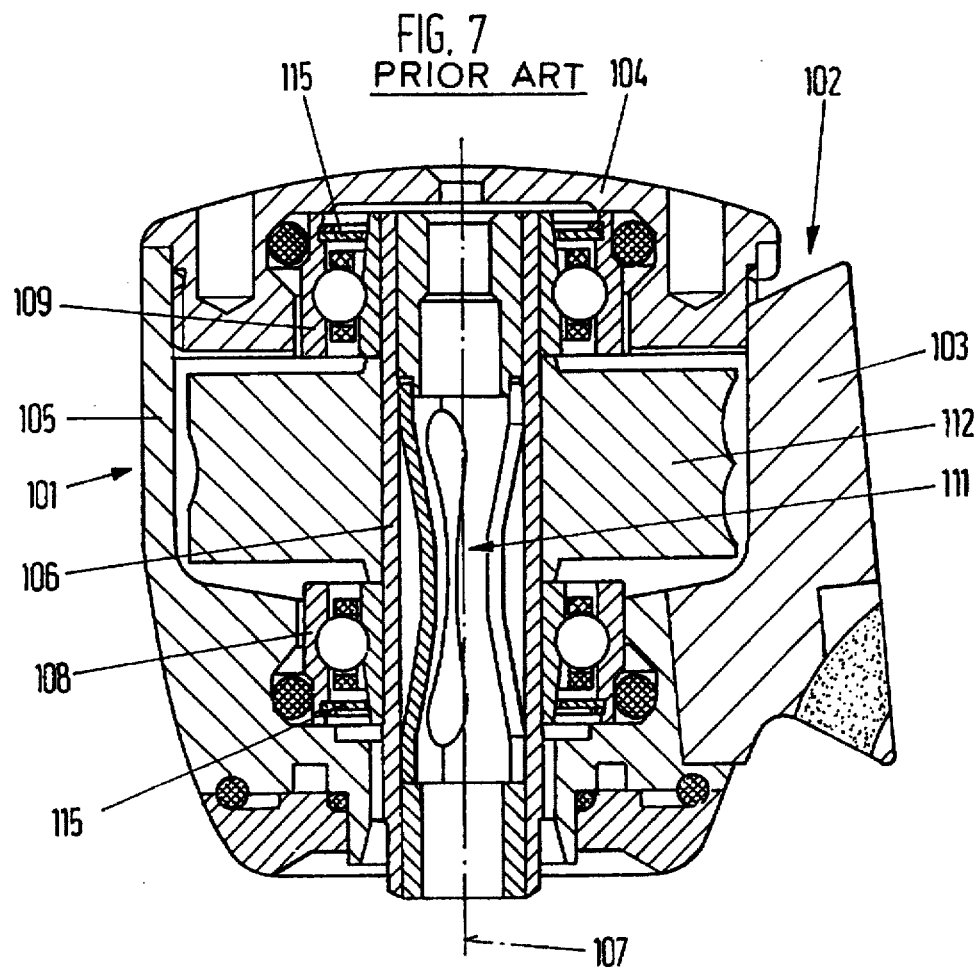

FIG. 7 shows the head 101 of a so-called angled handpiece 102 in axial section. To the handpiece 102 there belongs a grip sleeve 103, angled in the usual manner, of which only the forwardmost part is to be seen. In the housing 105 of the head 101, which housing is closed above by means of a lid 104, for example a screw-on lid, a hollow drive shaft 106 is mounted in two roller bearings 108, 109 freely rotatably around a rotation axis 107 extending transversely of the grip sleeve 103, of which roller bearings the roller bearing towards the tool is arranged in the region of the floor of the housing 105 and the roller bearing 109 away from the tool side is arranged in the lid 104. A tool (not shown) can be inserted by means of its shaft into the drive shaft 106, which drive shaft penetrates through the floor on the tool side in a hole, and the tool can be clamped in the inserted position by means of a clamping device 111. In the present configuration, the clamping device 111 is provided by means of several spring tongues in the hollow drive shaft 106 which tongues are, upon insertion of the tool shaft, bent away from one another and press radially inwardly against the shaft. Between the roller bearings 108, 109, a turbine wheel 112 is fixedly arranged on the drive shaft 106, towards which turbine wheel there is directed a compressed air channel (not shown) extending through the grip sleeve 103. For rotation of the mounted tool (not shown), the compressed air can be turned on by means of a switch which is likewise not shown.

Figure 8:
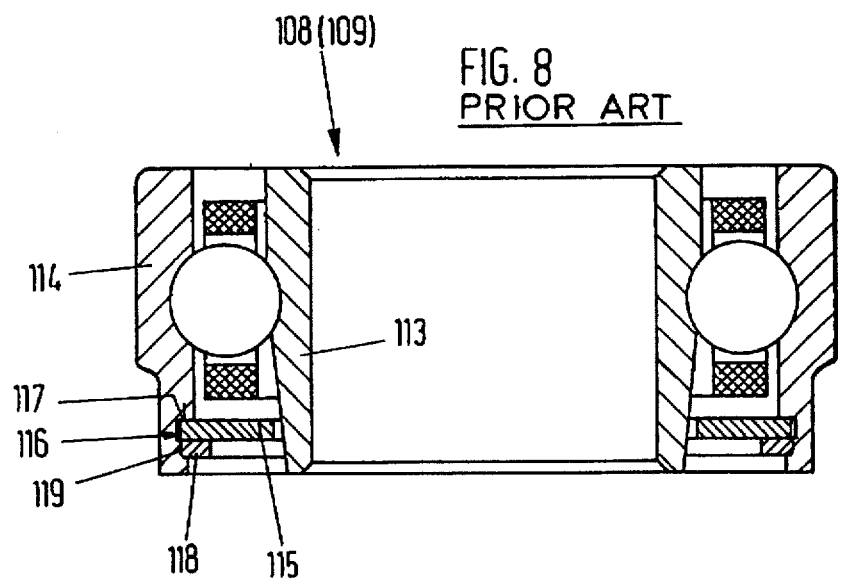

There is associated with each roller bearing 108, 109 a respective blocking or sealing disk 115 effective between the inner ring 113 and the outer ring 114, the configuration and arrangement of which disk can be seen from FIG. 8 which shows one of the two identical roller bearings 108, 109 in enlarged axial section. A difference between the roller bearings 108, 109 is found solely in that the associated sealing disk is arranged in each case outwardly on the associated roller bearing, which bearings are installed to mirror-image one another.

The sealing disk 115 is in each case set with its outer edge into a widened bore 116, with a matching fit, the disk bearing on inwardly on shoulder 117 of the widened bore 116 and being axially restricted outwardly by means of a spring ring 118 which is releasibly set into an internal angular groove 119 in the widened bore 116. The inner edge of the sealing disk 115 surrounds the outer surface of the inner ring 113 with a slight play for movement, whereby the external sealing of the roller bearing is provided.

This known configuration has proved itself in practice, but it can still be improved.

There is described in EP-0 527 423 A1 an angled dental drill handpiece in which a drive wheel arranged in the angled head of the handpiece is arranged with the associated roller bearing in a bearing sleeve which can be placed from above into the handpiece. For sealing the tool drive in the handpiece head there is provided between the bearing sleeve and a drive shaft which receives the drilling tool a labyrinth seal on the side of the handpiece head towards the tool. The labyrinth seal has an axially outer labyrinth ring and an axially inner labyrinth ring of which the outer is mounted on the drive shaft to rotate with the drive shaft and projects radially outwardly and of which the inner labyrinth ring projects from the bearing sleeve radially inwardly and is formed in one piece on the bearing sleeve, the outer labyrinth ring having a coaxially inwardly projecting hollow cylindrical annular section which engages over a hollow cylindrical annular section arranged on the inner labyrinth ring and projecting outwardly. Further, this labyrinth seal is surrounded by a protection sleeve which is set into the bearing sleeve, which protection sleeve covers over the outer labyrinth ring with radial spacing and has in the region of a radial step surface of the outer labyrinth ring a radial opening through which contaminant particles are intended to be radially outwardly ejected.

This known configuration is complicated, has many components and is expensive in manufacture.

The object of the invention is to prevent or to reduce the penetration of contaminants into the housing or into the roller bearing or bearings, with a medical or dental treatment instrument of the kind indicated in the introduction.

This object is achieved by the features of the invention described below in detail.

With the treatment instrument in accordance with a first embodiment the invention, the blocking ring bears against the inner ring with its surface towards the inner ring, and the blocking ring is releasibly or non-releasibly connected with the inner ring in a sealed manner. By these means there is provided a significantly improved barrier against the penetration of contaminants, because no seam or no movement gap is present between the blocking ring and the inner ring, through which seam or gap the contaminants could penetrate. Rather, the contaminants must pass radially around the blocking ring in order to get behind the blocking ring and thus into the roller bearing and/or into the housing.

The same advantages are attained when the blocking ring sits sealingly on the drive shaft, fixed for rotation with the drive shaft, in accordance with another embodiment of the invention.

The invention can provide a simple fixing of the blocking ring on the inner ring or outer ring which is protective for the roller bearing, whereby a stable and sealed fixing is achieved without there occurring, because of overheating, a distortion at the inner and outer ring which would affect the running of the roller bearing and its working life.

Also, it is known from DE-37 19 149 A1 to counter the above-described sucking-in effect with a turbine handpiece in that there is arranged in the compressed air line leading to the turbine a pressure store through which the compressed air flows and which also, after switching off of the compressed air supply, discharges into the housing air under pressure and thereby prevents the sucking-in upon running out of the turbine wheel, but this solution is however, on the one hand, applicable only when a turbine drive is present and, on the other hand, a considerable volume is needed for the pressure store which, in particular when such is to be arranged in the region of the treatment instrument, can be realised only with difficulty because of lack of available space and leads to other disadvantages.

With the configuration of another embodiment of invention, the desired goal is achieved by means of a labyrinth seal which both alone and also in combination with the other configurations leads to an advantageous sealing of the inner or bearing space. It is advantageous to so form the labyrinth seal that there is predetermined for penetrating contamination an S-like path running radially inwardly which provides an effective barrier against the penetration of contamination. Such a S-like labyrinth path can be formed by means of two hollow cylindrical labyrinth ring sections projecting axially towards one another, of which the labyrinth ring section arranged on the outer labyrinth ring and projecting inwardly engages over, with a gap, a labyrinth section arranged on the inner labyrinth and directed outwardly. Thereby, the axially inner labyrinth ring may be non-releasibly fixed in the head housing of the handpiece, for example by means of force fitting, gluing or by means of one-piece construction on the head housing.

All above-described embodiments according to the invention distinguish themselves by a simple and economically manufacturable construction. It is thereby possible, with all embodiments in accordance with the invention, to prefabricate at least one component of the embodiment according to the invention on its carrier or to pre-mount it on its carrier, whereby a significant simplification is achieved. This applies not only for the labyrinth seal in accordance with the invention but also for a blocking ring in accordance with the invention or a bladed wheel (impeller) for the ventilation device in accordance with the invention. These components can be completely prefabricated on a roller bearing and can thereby be simply manufactured and installed.

All of the embodiments in accordance with the invention achieve the object of the invention in an advantageous manner.

The subclaims contain features which provide for further improvement of the sealing and further simple and practical embodiments.

The embodiments in accordance with the invention are suitable preferably for a so-called turbine handpiece in which the drive shaft runs on after the switching off of the drive.

Thereby, the blocking ring or rings and/or the bladed wheel or bladed wheels (impellers) maybe arranged inwardly and/or outwardly on the associated roller bearing or may be fixed on the inner ring of the roller bearing.

The bladed wheel (impeller) can be comprise a ring and wings or blades projecting radially therefrom, the widths of the blades preferably diverging outwardly, in particular only on one side of the bladed wheel.

It is also possible, inwardly of the first blocking ring or bladed wheel, to arrange a second blocking ring which is arranged in particular on the opposing outer or inner ring of the associated roller bearing. Thereby, the second blocking ring can cooperate in a sealing manner with the inner ring or the sleeve. It is also of advantage to effect the arrangement such that a preferably radial sealing surface with which the first sealing ring sealingly cooperates is formed by a securing ring which restricts the second blocking ring on the side towards the first blocking ring.

Since, in particular with such a handpiece head which has an opening on its a side away from the tool, there is a danger of penetration of contamination also on this side, it is advantageous to arrange the features according to the invention also in the region of the handpiece away from the tool, in particular to form and prefabricate a roller bearing provided in this region in accordance with the invention.

The invention also relates to a roller bearing having the features in accordance with the invention, whereby the advantages described above are likewise achieved.

Figure 2:
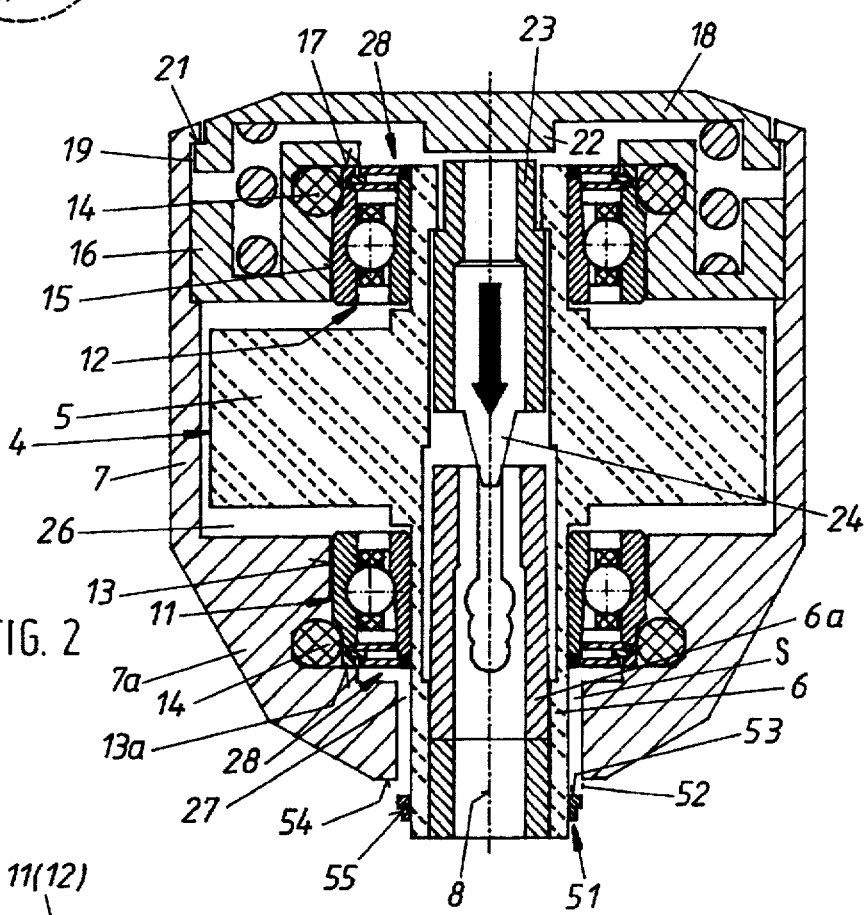
Figure 3:
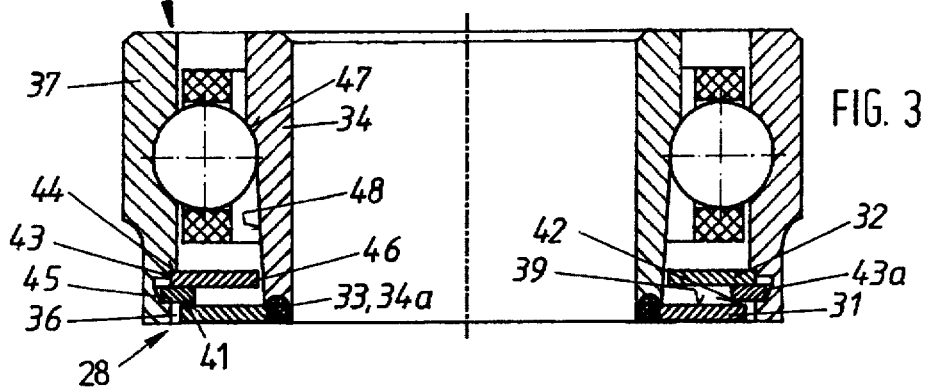
Figure 4:
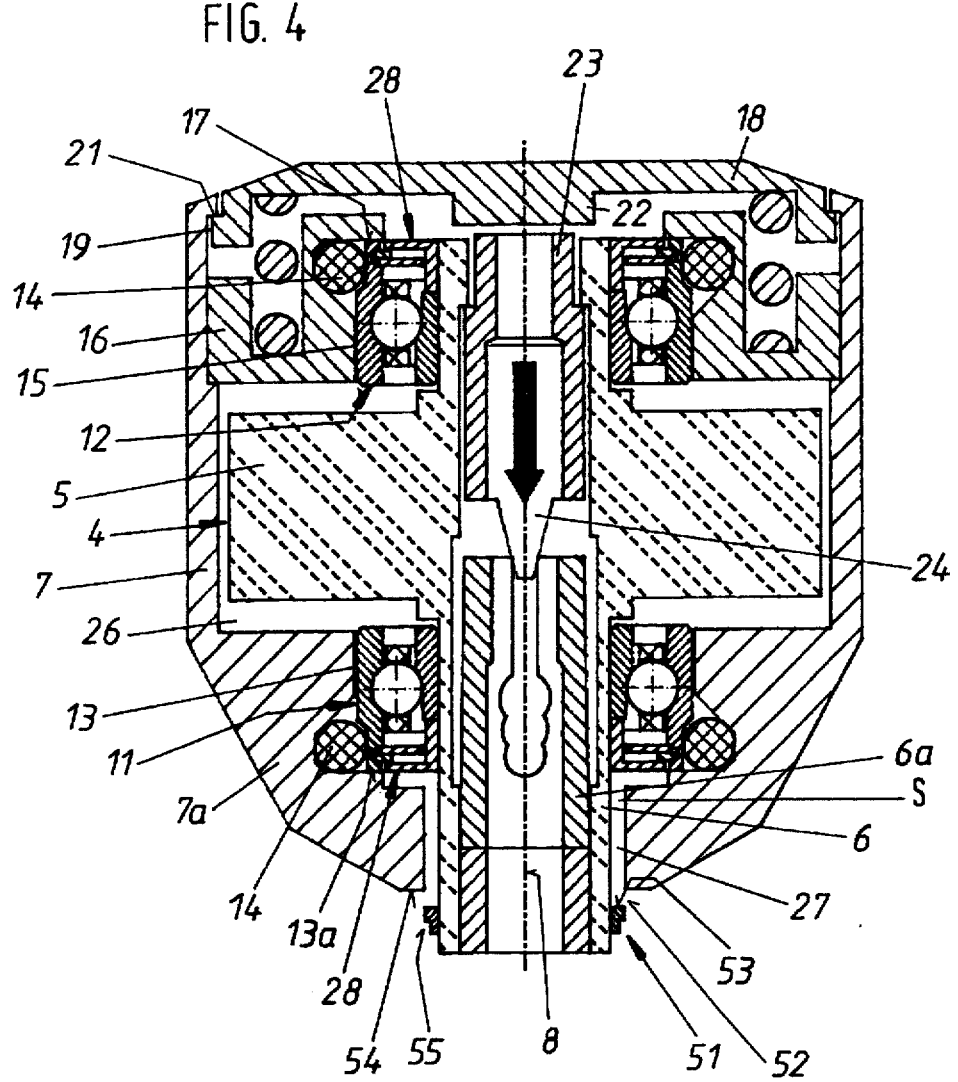
Figure 5:
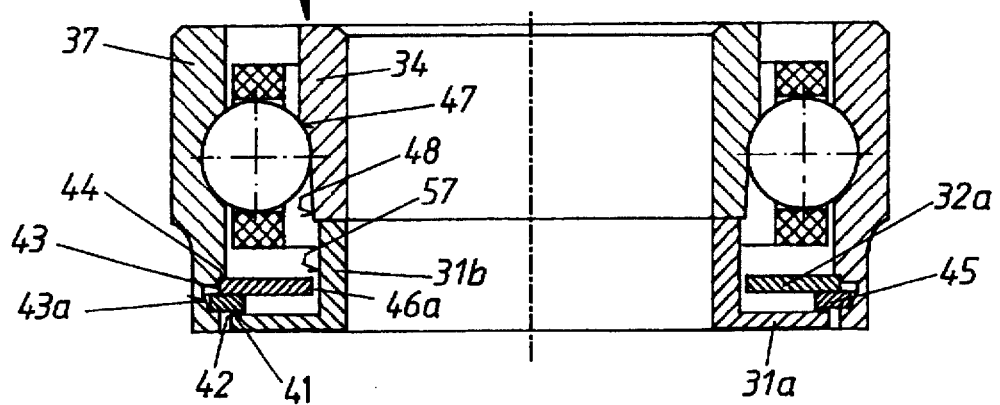
Figure 6:
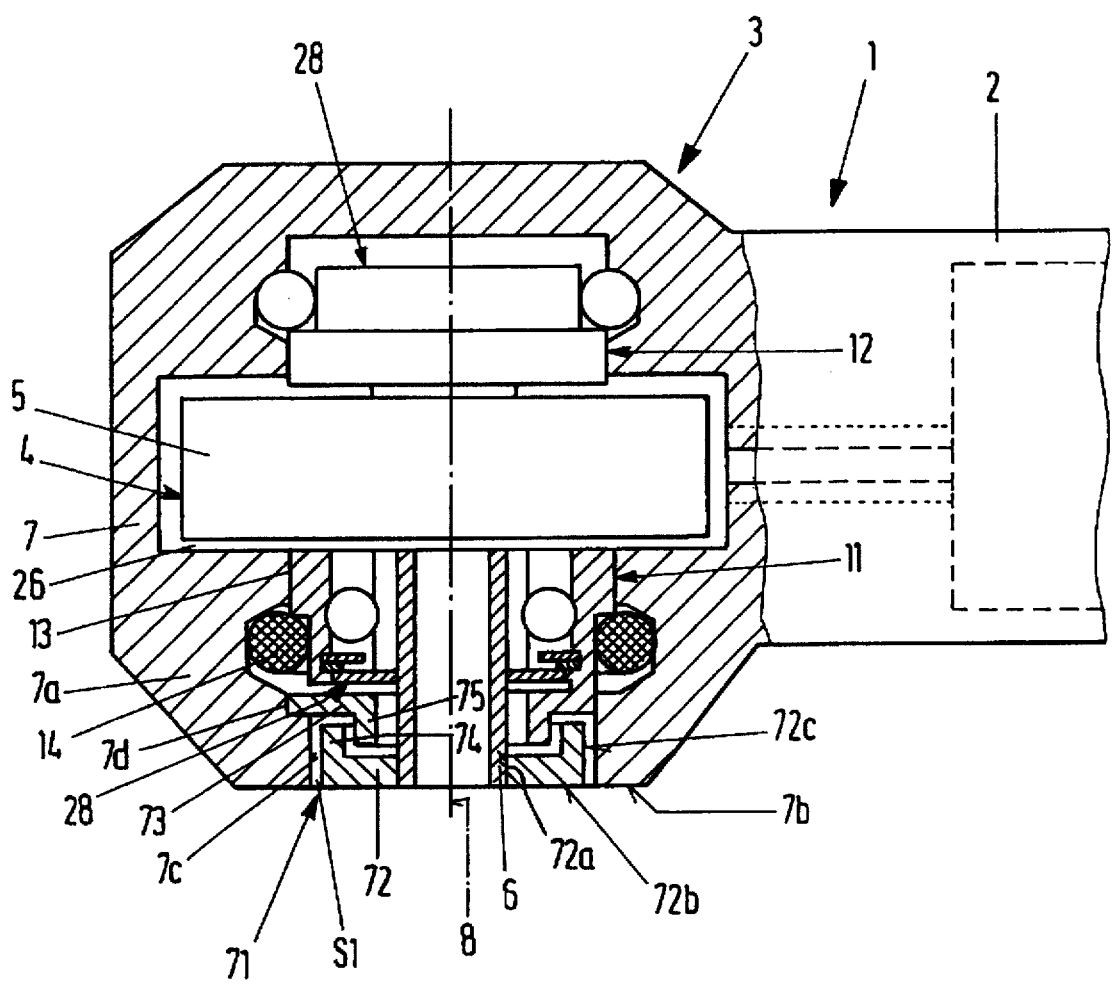

Below, the invention and further advantages achievable thereby will be described in more detail with reference to preferred embodiments and simplified drawings, which show;

FIG. 1 a treatment instrument in accordance with the invention, in the form of a so-called angled handpiece, in side view;

FIG. 2 the head of an angled handpiece with a turbine drive, in axial section;

FIG. 3 a roller bearing for the handpiece head, in enlarged sectional representation;

FIG. 4 in axial section, the head of a treatment instrument in accordance with the invention in the form of an angled handpiece having turbine drive, in a modified configuration;

FIG. 5 a roller bearing in the head of the turbine handpiece of FIG. 4, in enlarged sectional representation;

FIG. 6 a detail of the treatment instrument, in a further modified configuration;

FIG. 7 the head of a known angled handpiece with a turbine drive, in axial section;

FIG. 8 a known roller bearing for the headpiece of FIG. 7, in enlarged sectional representation.

The main parts of the angled handpiece—generally designated by 1—are a grip sleeve 2 formed angled in conventional manner, a so-called angled head 3 attached to the forward end of the grip sleeve, a drive turbine 4 arranged in the angled head and having a turbine wheel 5, and a drive shaft 6 which is mounted in the housing 7 of the angled head 3 to be rotatable about an axis of rotation 8 extending transversely of grip sleeve 2, by means of the drive turbine 4. A chuck sleeve 6a is attached in the drive shaft 6, into which chuck sleeve a treatment tool (not shown) can be inserted from the tool side of the angled head 3 and held in place.

In the present embodiment, the turbine handpiece 1 is only a part, namely the forward part, of a treatment instrument having a so-called supply part (not shown) which is releasibly connectible with the rearward end of the turbine handpiece 1 or the grip sleeve 2, preferably by means of a per se known plug-in twist coupling 9. Longitudinally through the grip sleeve 2 there extend supply lines (not shown), such as a compressed air line which extends up to the drive turbine 4, and further lines for light, air and cooling or treatment fluids or spray, which open in the forward region of the grip sleeve 2 in a direction towards the treatment site. When a plug-in/twist coupling 9 is provided, the above-mentioned lines extend through this coupling and are taken further in the supply part and connected to a supply device (not shown).

As can be appreciated from FIG. 2, two roller bearings 11, 12 are provided for mounting the drive shaft 6, which roller bearings are formed identically one to another but arranged in mirror image fashion one to the other. The roller bearing 11 to the tool side is set in an inner bearing bore 13 in the floor part 7a of the housing 7 and is sealed at the periphery by means of a sealing ring 14 whereby the roller bearing bears against an internal shoulder 13a of the bearing bore 13 with its end face towards the tool side.

The roller bearing 12 away from the tool is seated in a bearing bore 15 of a bearing disk 16 which is set in the housing 7 from the side away from the tool and is fixed in a manner not illustrated. The roller bearing 12 away from the tool abuts against an internal shoulder 17 of the bearing disk 16 with its end face away from the tool, and is therein sealed by means of a sealing ring 14 which bears against its external surface. The housing 7 is closed by means of a lid 18 on its side away from the tool, which lid is displaceable in an axial guide 19 effective between itself and the housing 7 and is biassed into its end position away from the tool, against a movement stop 21 on the housing 7, by means of a compression spring 20 effective between itself and the housing 7 or the bearing disk 16. The lid 18 has, on the inner side, in its center, a pressure piece 22 which, upon pressing-in of the lid 18 by means of a finger of the operating hand, displaces inwardly plunger 23 mounted axially displaceably in the drive shaft 6, which plunger is—with a release wedge 24 arranged at its end towards the tool—able to release a tool (not shown) which is inserted from the tool side into the chuck sleeve 6a set in the drive shaft 6.

The turbine wheel 5 is arranged on the drive shaft 6 between the roller bearings 11, 12 and is rotatable in a free space 26 of the housing 7 by means of the above-described compressed air drive. In the present embodiment, the turbine wheel 5 is formed in one piece with the drive shaft 6. The latter extends through a bore 27—which is reduced with respect to the bearing bore 13—in the floor part 7a to the outside, whereby the drive shaft may project outwardly beyond the floor part 7a or may alternatively end level with the tool side of the floor part 7a.

As can be appreciated from FIGS. 2 and 3, the roller bearing 11 near to the tool is sealed on its side near to the tool, and the roller bearing 12 away from the tool is sealed on its side away from the tool each by means of otherwise identical axial seal 28 which preferably forms a labyrinth seal.

The seal 28 comprises in each case two disk-like blocking rings or sealing rings 31, 32 arranged axially one behind the other, which in the present embodiment are each formed by means of a flat annular disk. The outer sealing ring 31 is fastened to the inner ring 34 by laser spot welding 33, whereby the outer sealing ring 31 preferably bears flatly against the outer end surface 34a of the inner ring 34. The outer edge of the outer sealing ring 31 cooperates sealingly with the outer ring 37, with the formation of a seal seam 36, whereby the cylindrical peripheral surface of the outer sealing ring 31 may cooperate with the cylindrical inner surface of the outer ring 37, with the formation of an axial seal seam with slight play for movement, and/or the outer sealing ring 31 may cooperate with its inner end surface 39 with an outwardly directed approximately radial sealing surface 42 of the outer ring 37, with the formation of a seal seam 41. In the present embodiment, the radial sealing surface 42 is a shoulder surface projecting inwardly from the outer ring 37, which shoulder surface has a spacing from the end face of the outer ring 37 on the tool side so that the outer sealing ring 31 is arranged sunken into the outer ring 37 and on the tool side preferably ends on a level with the end face of the outer ring 37.

Preferably, the sealing ring 31 is part of a labyrinth seal having a second sealing ring 32 preferably arranged inwardly of the sealing ring 31, which second sealing ring sits in a bore widening internal circumferential groove 43 bearing inwardly against a shoulder surface 44 and being restricted outwardly by means of a releasable securing ring 45 which is seated in an inner groove 43a. As is the outer sealing ring 31, the inner sealing ring 32 is also formed by means of a flat annular disk. Further, in the present embodiment, the sealing surface 42 which radially cooperates with the outer sealing ring 31 is formed by the outer side of the flat securing ring 45 so that it needs no particular shoulder surface. For receiving the inner blocking ring or sealing ring 32 and the securing ring 34 there is provided a common, stepped inner peripheral groove. The free internal cross-section of the inner blocking ring or sealing ring 32 is so adapted to the outer cross-section of the inner ring 34 that between the two approximately cylindrical seal surfaces there is a seal seam 46 with slight play for movement.

In the present embodiment the roller bearings 11, 12 are each formed by a ball groove bearing, whereby the ball groove 47 in the inner ring 34 is open on the outside. In the present embodiment the ball groove 47 adjoins a conical surface 48 of slight inclination, diverging towards the ball groove, which conical surface forms the outer surface of the inner ring 34 and also the sealing surface for the inner sealing ring 32. Preferably, the inner peripheral surface of the inner blocking ring or sealing ring 32 is adapted to the inclination of the conical surface 48.

The above-described arrangement of the outer sealing ring 31 also prevents an unintended dismounting of the associated roller bearings 11, 12. Thus, upon dismounting of the drive shaft 6 there is no need to pay attention to preventing the roller bearings 11, 12 from falling apart.

The roller bearing 12 away from the tool is, taking into account its mirror-image arrangement, correspondingly arranged and formed, so that a separate description thereof is not needed.

The sealing of the roller bearing 11 on the tool side can be effected, or improved additionally to the above-described sealing, in that there is fixedly arranged on the drive shaft 6 before the roller bearing 11 or behind the roller bearing 12, a centrifugal ring 51 or a centrifugal disk, which preferably cooperates with a surface of the housing 7 or an attachment thereof with the formation of a seal seam 52 with slight play for movement. In the present embodiment, the end surface of the centrifugal ring 51 away from the tool is a first sealing surface 53 which cooperates with a second sealing surface 54 of the housing 7, which second sealing surface is preferably the outer surface of the housing 7 towards the tool. The centrifugal ring 51 represents a considerable obstacle for contaminant materials which creep axially on the outer surface of the drive shaft 6 in the direction towards the roller bearing 11 towards the tool, because the contaminant materials are radially deflected and because of the increase in centrifugal force which thereby takes place are centrifugally ejected. Such materials, in particular fluids, which adhere to the centrifugal ring 51 despite this centrifugal effect and might creep further in the direction towards the roller bearing 11 find a barrier on the side of the centrifugal ring 51 away from the tool which can scarcely be overcome because the contaminant material would have to creep radially inwardly against the radially outwardly effective centrifugal force on the centrifugal ring 51, which is scarcely possible. Furthermore, the inwardly directed further creeping movement is prevented by means of the seal seam 52. It is of advantage to provide the centrifugal ring 51 with a peripheral groove 55 on its side towards the tool, so that the centrifugal ring is given an angled cross-sectional form. By these means a further barrier is created which further prevents the creeping of contaminant materials.

The embodiments according to FIGS. 4 and 5, in which the same or similar parts are given the same reference signs, differs from the above-described embodiment in that the sealing ring 31a, corresponding to the sealing ring 31, is not attached to the inner ring 34 but sits fixedly on the drive shaft 6, whereby it preferably bears against the side of the inner ring 34 facing it. If, on the tool side, the sealing ring 31a ends on a level with the end surface of the outer ring 37, the inner ring 34 is shorter than the outer ring 37 in correspondence to the axial dimension of the sealing ring 31a. In the present embodiment the sealing ring 31a is arranged, preferably in one piece, in particular on the end of a short sleeve 31b towards the tool, which short sleeve ensures a secure seating on the drive shaft 6 and which bears against the inner ring 34 with its end away from the tool. The latter is correspondingly shorter.

If the sealing ring 31a is provided with an inwardly directed, preferably hollow cylindrical sleeve 31b, it is of advantage to allow the inner sealing ring 32a to cooperate sealingly with the outer surface 57 of the sleeve 31b at a seal seam 46a with little play for movement, whereby there can be realized in this case cylindrical sealing surfaces.

In the case of attachment by welding, the outer sealing ring 31 is of a steel which can be welded to the inner ring 34—the outer sealing ring can also be of plastics material when another of the indicated forms of attachment is used. The inner sealing ring 32 and/or the outer sealing ring 31a with the sleeve 31b can likewise be of steel or of plastics material.

In the embodiment according to FIG. 6, in which the same or similar parts are likewise given the same reference signs, a labyrinth seal 71 is arranged between the wall 7a of the housing 7 on the tool side on the drive shaft 6, which labyrinth seal forms an effective barrier against in particular solid contaminant parts and also against non-solid contaminant such as fluids. The labyrinth seal 71 has two labyrinths-rings 72, 73 which engage over one another axially and preferably also radially. The labyrinth rings 72, 73 are of plastics material or preferably of metal, in particular steel. The axially outer labyrinth ring 72 is arranged fixedly on the drive shaft 6 with an appropriate bore 72a and is attached for example by means of being forced on, by gluing or by welding. Thereby, it is advantageous to arrange this labyrinth ring 72 on the drive shaft 6 so that its outer side surface 72a ends approximately at the level of the side surface 7b of the housing 7 on the tool side. In the region of the axially outer labyrinth ring 72 the bore 7c present in the housing wall 7a is larger than usual and is dimensioned with such a radial spacing from the drive shaft 6 that a slight gap is present between the cylindrical peripheral surface 72c of the labyrinth ring 72 and the cylindrical wall of the bore 7c.

The axially outer labyrinth ring 72 forms with its outer side surface 72b a centrifugal surface on which, upon rotation of the drive shaft with the tool, contaminants are radially centrifugally ejected. It is thus also a centrifugal ring.

The axially inner labyrinth ring 73 is attached non-rotatably to the housing wall 7a, for example arranged in one piece, or seated in a corresponding receiving hole and attached therein for example by pressing, gluing or welding. The labyrinth ring 73 can be set into the bore 7c. In the present embodiment, there is provided a step-like bore widening 7d into which the labyrinth ring 73 is fixedly set with its outer peripheral surface. Between the labyrinth rings 72, 73 there is likewise provided a slight radial gap S1 by which the labyrinth is formed. Preferably the axially outer labyrinth ring 72 has on its outer periphery, and the axially inner labyrinth ring 73 has on its inner periphery, in each case a sleeve-like preferably hollow cylindrical axial ring extension 74, 75 which ring extensions stand up axially towards one another and overlap, whereby the ring extension 74 of the axially forward labyrinth ring 72 engages over the ring extension 75 of the axially inner labyrinth ring 73 with a radial spacing forming the gap S1. Thereby, between the ring extension 75 and labyrinth ring 72 there is likewise present the gap S1 extending here radially, which gap also continues inwardly between the axially inner labyrinth ring 73 and the drive shaft 6 and here, if appropriate, is of somewhat larger dimensions. By these means there is provided an S-like axially and radially inwardly running labyrinth path.

The above-described labyrinth seal 71 or another labyrinth seal is very suitable in combination with an axial sealing or covering of the associated roller bearing 11, as shown by FIG. 6.

In FIG. 6, right hand half, there is shown a modified configuration or arrangement of the axially inner labyrinth ring 73. In this modification, the labyrinth ring 73 is arranged in one piece on the outer ring of the roller bearing 11 present, here by means of an axially and correspondingly angled running extension of the outer ring. With this configuration, the labyrinth ring 73 can be prefabricated on the roller bearing 11 and mounted together with the roller bearing.

As for the above-described exemplary embodiments it is advantageous also for this embodiment to provide the bearing 12 away from the tool also with a corresponding sealing or covering 28, in mirror-image fashion, in order to prevent or reduce on this side also the penetration of contamination. This is particular with the case for such housings 7 as have on their side away from the tool a closable or permanently open opening.

With the embodiment according to FIG. 6 also—as already in accordance with FIG. 2—the drive shaft 6 preferably with the turbine wheel 5 and the roller bearings 11, 12 can be installable and dismountable from the side away from the tool.

The blocking rings 31, 31a may be of plastics material or preferably of metal or steel, whereby they abut sealingly with their peripheral sections against the associated abutting parts and thus can form a sealing disk or they form blocking disks the blocking peripheral sections of which have a slight axial or radial spacing (play) from the neighbouring components and thus define a gap, whereby a covering or a labyrinth gap is provided.

With reference to the present drawings, the above-described measures in accordance with the invention have been described with regard to a treatment instrument having a turbine as drive for the drive shaft. Within the scope of the invention it is, however, also possible and advantageous to employ the measures for preventing or reducing the penetration of contamination into the housing 7 or into the bearing sites with a treatment instrument not having a turbine drive in the head region, for example a treatment instrument having a mechanical drive connection running in the head region. The desired advantages are achieved with the features in accordance with the invention also in the case of such treatment instruments.

Further, it is to be emphasized that diverse parts of the configurations in accordance with the invention have the same or similar functions or functionally combine or supplement one another. For example, the sealing ring 31 or 31a form in each case a blocking or centrifugal ring because they are directly or indirectly connected with the drive shaft 6 and thus are subjected to rotation. It is therefore of advantage to provide radial dimensions of the sealing ring 31 or 31a as great as possible and to form them in the shape of disks so that a considerable centrifugal effect is achieved.

Furthermore, the centrifugal ring 51 effects a sealing function, in the sense of a sealing ring or of a sealing disk, if it cooperates sealingly with the housing 7 or with an attachment to the same, i.e. when it forms sealing surface. Thus, the sealing rings 31 also fulfil a centrifugal function.

Furthermore, it is to be emphasized that both the sealing rings 31, 31a, 32 and/or the centrifugal ring or rings 51 form a labyrinth seal which likewise contributes to the present solution.

We claim:

1. A medical or dental treatment instrument comprising a handpiece (1) and a drive shaft (6) for a tool, said drive shaft (6) being mounted in a forward housing (7) of the instrument and being drivable by drive means, at least one roller bearing (11, 12) rotatable about a middle axis and disposed around said shaft (6), wherein said drive shaft (6) penetrates an associated wall (7a) of the housing (7) in a hole (7c, 27) and wherein said roller bearing (11, 12) is blocked against contaminants by means of a first blocking ring (31) effective between an outer ring (37) associated with the housing (7) and an inner ring (34) able to rotate with said drive shaft (6), wherein said first blocking ring (31) is formed by an annular disk and has an inner radial surface facing and in contact with said inner ring (34), the inner ring (34) having an outer radial surface and the outer ring (37) having an inner radial surface, and wherein:

the first blocking ring (31) is non-releasably attached on the outer radial surface of the inner ring (34); the outer ring (37) has a radial inner shoulder (42) projecting therefrom and having an inner end portion opposite the inner surface of outer ring (37); and the end portion of the shoulder (42) overlaps an outer end portion of the first blocking ring (31).

2. Treatment instrument according to claim 1 wherein the blocking ring (31) cooperates sealingly with the outer ring (37).

3. Treatment instrument according to claim 1 wherein the blocking ring (31) is disposed outwardly of the at least one roller bearing.

4. The medical or dental treatment instrument according to claim 1, wherein the blocking ring (31) is attached to the outer surface of the inner ring (34) by means selected from the group consisting of gluing, welding, and screwing.

5. Treatment instrument according to claim 4 wherein the blocking ring (31) is attached to the outer surface of the inner ring (34) by means of laser spot welding.

6. The medical or dental treatment instrument according to claim 1, wherein the inner shoulder (42) comprises a releasable securing ring (45) seated in an inner groove (43a), and further comprising a second blocking ring (32) disposed in an inner peripheral groove (43).

7. The medical or dental treatment instrument according to claim 6, wherein the second blocking ring (32) and the first blocking ring (31) are made from a material selected from the group consisting of steel and plastic.

8. The medical or dental treatment instrument according to claim 1, wherein the blocking ring (31) cooperates sealingly with the inner shoulder surface (42).

9. The medical or dental treatment instrument according to claim 1, wherein at a spacing from a first roller bearing (11) directed toward the side away from the tool a second roller bearing (12) is provided for the drive shaft (6), said second roller bearing (12) being designed mirror-symmetrically with respect to a middle axis extending at right angles to the drive shaft (6).

10. The medical or dental treatment instrument according to claim 1, further comprising:

a labyrinth seal (71) disposed between the wall (7a) of the housing (7) and the drive shaft (6), said labyrinth seal comprising two labyrinth rings (72, 73) having ring extensions (74, 75) extending axially toward one another and defining at least one radial gap between said rings (72, 73), wherein one of said labyrinth rings (72) is associated with the drive shaft (6) the other labyrinth ring (73) is disposed in one piece on an outer ring of the roller bearing (11, 12), and wherein the labyrinth rings (72, 73) overlap both radially and axially.

11. The medical or dental treatment instrument according to claim 1, wherein the handpiece (1) is an elongate, angled structure.

12. The medical or dental treatment instrument according to claim 1, further comprising turbine drive means.

13. The medical or dental treatment instrument according to claim 1, wherein the outer radial surface of the inner ring (34) is at an angle to, and projects inwardly toward the tool end with respect to, the inner surface of the outer ring (37).

14. The medical or dental treatment instrument according to claim 1, further comprising:

a labyrinth seal (71) disposed between the wall (7a) of the housing (7) and the drive shaft (6), said labyrinth seal comprising two labyrinth rings (72, 73) having ring extensions (74, 75) extending axially toward one another and defining at least one radial gap between said rings (72, 73), wherein one of said labyrinth rings (72) is associated with the drive shaft (6) the other labyrinth ring (73) is disposed in one piece on an outer ring of the roller bearing (11, 12), and wherein the labyrinth rings (72, 73) overlap both radially and axially.

15. Treatment instrument according to claim 14 wherein said labyrinth rings are attached to their respective carrying parts by laser spot welding.

16. The medical or dental treatment instrument according to claim 14, wherein:

said labyrinth rings (72, 73) define an S-like gap (S1) therebetween; and an axially outer side surface (72a) of the first labyrinth ring (72) ends approximately at the level of a side surface (7b) of the housing (7) on the tool side.

17. A medical or dental treatment instrument comprising a handpiece (1) and a drive shaft (6) for a tool, said drive shaft (6) being mounted in a forward housing (7) of the instrument and being drivable by drive means, at least one roller bearing (11, 12) rotatable about a middle axis and disposed around said shaft (6), wherein said roller bearing (11, 12) penetrates an associated wall (7a) of the housing (7) in a hole (7c, 27) and wherein said roller bearing (11, 12) is blocked against contaminants by means of a first blocking ring (31) effective between an outer ring (37) associated with the housing (7) and an inner ring (34) able to rotate with said drive shaft (6), wherein said first blocking ring (31) is formed by an annular disk and has an inner radial surface facing and in contact with said inner ring (34), the inner ring (34) having an outer radial surface and the outer ring (37) having an inner radial surface, and wherein:

- the blocking ring (31a) is disposed on a sleeve (31b) comprising a radial disk, said disk (31b) bearing against a side of the inner ring (34) and being associated with the drive shaft (6) fixed for rotation therewith; the outer ring (37) has a radial inner shoulder (42) projecting inwardly; and an inner end portion of the shoulder (42) overlaps an outer end portion of the blocking ring (31a).

18. The medical or dental treatment instrument according to claim 17, further comprising:

- a labyrinth seal (71) disposed between the wall (7a) of the housing (7) and the drive shaft (6), said labyrinth seal comprising two labyrinth rings (72, 73) having ring extensions (74, 75) extending axially toward one another and defining at least one radial gap between said rings (72, 73), wherein one of said labyrinth rings (72) is associated with the drive shaft (6) the other labyrinth ring (73) is disposed in one piece on an outer ring of the roller bearing (11, 12), and wherein the labyrinth rings (72, 73) overlap both radially and axially.

19. The medical or dental treatment instrument according to claim 17, wherein the inner shoulder (42) comprises a releasable securing ring (45) seated in an inner groove (43a), and further comprising a second blocking ring (32) arranged in an inner peripheral groove (43).

20. The medical or dental treatment instrument according to claim 19, wherein the second blocking ring (32) and the first blocking ring (31) are made from a material selected from the group consisting of steel and plastic.

21. A roller bearing assembly (11, 12) for a treatment instrument, comprising:

- an outer ring (37) able to be associated with a housing (7), said outer ring having a radially inner surface;
- an inner ring (34) able to rotate with said drive shaft (6), the inner ring (34) having a radially outer surface facing said inner surface of said outer ring (37);
- a ball groove bearing (47) disposed between said outer ring (37) and said inner ring (34) and disposable around a rotatable drive shaft (6);
- a blocking ring (31) effective between said outer ring (37) and said inner ring (34), said blocking ring (31) comprising an annular disk having a radially inner surface facing and in contact with said inner ring (34), wherein:
  - the blocking ring (31) is non-releasably attached on the outer surface of the inner ring (34); the outer ring (37) has a radial inner shoulder (42) projecting therefrom and having an inner end portion opposite the inner surface of outer ring (37); and the end portion of the shoulder (42) overlaps an outer end portion of the blocking ring (31).

22. The roller bearing assembly according to claim 21, wherein the inner shoulder (42) comprises a releasable securing ring (45) seated in an inner groove (43a), and further comprising a second blocking ring (32) arranged in an inner peripheral groove (43).

* * * * *